(12) United States Patent
Constantz et al.

(10) Patent No.: US 10,022,471 B2
(45) Date of Patent: *Jul. 17, 2018

(54) CALCIUM PHOSPHATE CEMENTS AND METHODS FOR USING THE SAME

(71) Applicant: Skeletal Kinetics, LLC, Cupertino, CA (US)

(72) Inventors: Brent R. Constantz, Portola Valley, CA (US); David Delaney, Capitola, CA (US); Duran N. Yetkinler, San Jose, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 983 days.

This patent is subject to a terminal disclaimer.

(21) Appl. No.: 13/800,694

(22) Filed: Mar. 13, 2013

(65) Prior Publication Data

US 2013/0273118 A1  Oct. 17, 2013

Related U.S. Application Data

(63) Continuation of application No. 11/189,555, filed on Jul. 25, 2005, now Pat. No. 8,419,803, which is a
(Continued)

(51) Int. Cl.
*A61L 27/12* (2006.01)

(52) U.S. Cl.
CPC ........... *A61L 27/12* (2013.01); *Y10S 514/951* (2013.01); *Y10S 514/955* (2013.01)

(58) Field of Classification Search
None
See application file for complete search history.

(56) References Cited

U.S. PATENT DOCUMENTS

| 4,160,012 A | 7/1979 | Ono et al. |
| 4,161,511 A | 7/1979 | Shiraki et al. |

(Continued)

FOREIGN PATENT DOCUMENTS

| EP | 0945147 A2 | 9/1999 |
| FR | 2805747 A1 | 9/2001 |

(Continued)

OTHER PUBLICATIONS

Lewis et al. (J. Biomed Mater Res. 2002, 63:191-199).*

(Continued)

*Primary Examiner* — Ernst V Arnold
(74) *Attorney, Agent, or Firm* — Norton Rose Fulbright US LLP

(57) ABSTRACT

Methods and compositions for producing flowable compositions, e.g. pastes, that set into calcium phosphate products are provided. In the subject methods, dry reactants that include a calcium source and a phosphate source are combined with a setting fluid to produce the flowable composition. A feature of the subject methods is that the dry reactants include a particulate calcium and/or phosphate reactant having a mean particle size of less than about 8 μm and narrow size distribution. Also provided are the compositions themselves as well as kits for use in practicing the subject methods. The subject methods and compositions produced thereby find use in a variety of applications, including the repair of hard tissue defects, e.g., bone defects.

27 Claims, 3 Drawing Sheets

Related U.S. Application Data continuation-in-part of application No. 10/900,029, filed on Jul. 26, 2004, now Pat. No. 7,175,858.

(56) References Cited

U.S. PATENT DOCUMENTS

| | | |
|---|---|---|
| 4,429,691 A | 2/1984 | Niwa et al. |
| 4,497,075 A | 2/1985 | Niwa et al. |
| 4,718,910 A * | 1/1988 | Draenert ............... 623/23.62 |
| 4,990,163 A | 2/1991 | Ducheyne et al. |
| 5,281,265 A | 1/1994 | Liu |
| 5,525,148 A | 6/1996 | Chow et al. |
| 5,545,254 A | 8/1996 | Chow et al. |
| 5,571,493 A | 11/1996 | Fulmer et al. |
| 5,580,623 A | 12/1996 | Fulmer et al. |
| 5,679,294 A | 10/1997 | Umezu et al. |
| 5,695,729 A | 12/1997 | Chow et al. |
| 5,697,981 A | 12/1997 | Ison et al. |
| 5,709,742 A | 1/1998 | Fulmer et al. |
| 5,795,922 A | 8/1998 | Demian et al. |
| 5,900,254 A | 5/1999 | Constantz |
| 5,954,867 A | 9/1999 | Chow et al. |
| 5,962,028 A | 10/1999 | Constantz |
| 5,968,253 A | 10/1999 | Poser et al. |
| 5,976,234 A | 11/1999 | Chow et al. |
| 5,997,624 A | 12/1999 | Chow et al. |
| 6,005,162 A | 12/1999 | Constantz |
| 6,027,742 A | 2/2000 | Lee et al. |
| 6,139,578 A | 10/2000 | Lee et al. |
| 6,719,993 B2 | 4/2004 | Constantz |
| 2005/0147551 A1 | 7/2005 | Tofighi et al. |

FOREIGN PATENT DOCUMENTS

| | | |
|---|---|---|
| JP | 2001106638 A | 4/2001 |
| JP | 2001518359 A | 10/2001 |
| JP | 2003516190 A | 5/2003 |
| JP | 2003531798 A | 10/2003 |
| JP | 2009506588 A | 2/2009 |
| WO | 2002036518 A1 | 5/2002 |

OTHER PUBLICATIONS

Bohner et al. "Technological Issues for the Development of More Efficient Calcium Phosphate Bone Cements: A Critical Assessment," (2005) Biomaterials, 26:6423-6429.

Merriam-Webster's Collegiate Dictionary tenth edition 1995, p. 212.

* cited by examiner

CALCIUM PHOSPHATE CEMENTS AND METHODS FOR USING THE SAME

CROSS-REFERENCE TO RELATED APPLICATIONS

This application is a continuation of application Ser. No. 11/189,555 filed on Jul. 25, 2005, issued as U.S. Pat. No. 8,419,803 on Apr. 16, 2013, which is a continuation-in-part of application Ser. No. 10/900,029 filed on Jul. 26, 2004, issued as U.S. Pat. No. 7,175,858 on Feb. 13, 2007; the disclosures of which are herein incorporated by reference.

INTRODUCTION

Background

Calcium phosphate cements hold great promise for use as structural materials in the orthopedic and dental fields. Such cements are typically prepared by combining a dry component(s) and a liquid to form a flowable paste-like material that is subsequently capable of setting into a solid calcium phosphate product. Materials that set into solid calcium phosphate mineral products are of particular interest as is such products can closely resemble the mineral phase of natural bone and are susceptible to remodeling, making such products extremely attractive for use in orthopedics and related fields.

While, a large number of different calcium phosphate cement formulations have been developed, there is a continued need for the development of yet more advanced formulations.

Relevant Literature

United States patents of interest include: U.S. Pat. Nos. 6,719,993; 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 4,161,511 and 4,160,012.

SUMMARY OF THE INVENTION

Methods and compositions for producing flowable compositions, e.g., pastes or clay-like compositions, which set into calcium phosphate products are provided. In the subject methods, dry reactants that include a calcium source and a phosphate source are combined with a setting fluid to produce the flowable composition. A feature of the subject methods is that the dry reactants include a particulate calcium and/or phosphate reactant having a mean particle size of less than about 8 μm and narrow size distribution. Also provided are the compositions themselves as well as kits for use in practicing the subject methods. The subject methods and compositions produced thereby find use in a variety of applications, including the repair of hard tissue defects, e.g., bone defects.

DESCRIPTION OF THE SPECIFIC EMBODIMENTS

Figure 1:
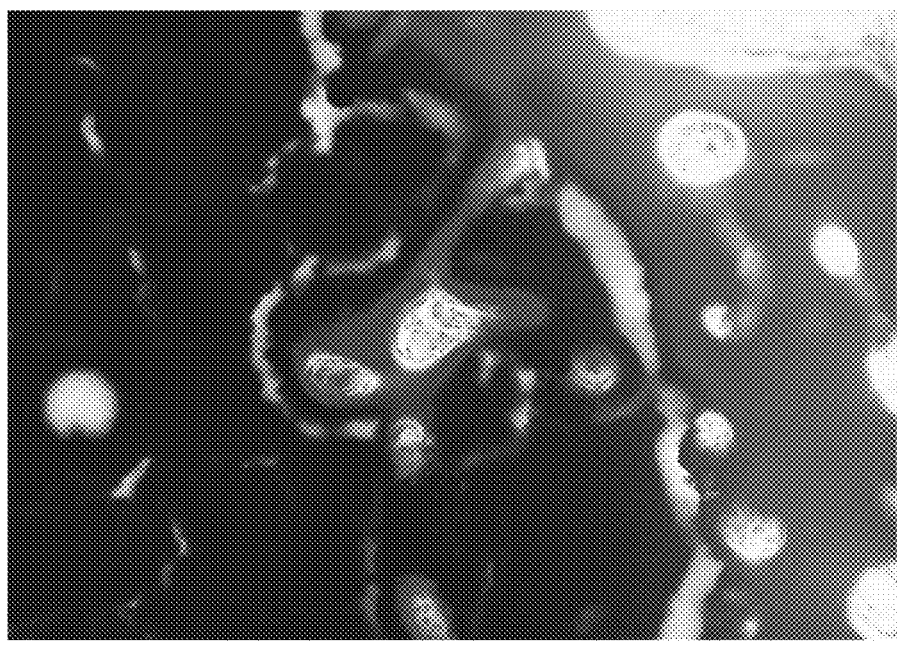
FIG. 1 provides a digital photograph of an implanted calcium phosphate cement according to an embodiment of the present invention.

Methods and compositions for producing flowable compositions, e.g., pastes or clay-like compositions, which set into calcium phosphate products are provided. In the subject methods, dry reactants that include a calcium source and a phosphate source are combined with a setting fluid to produce the flowable composition. A feature of the subject methods is that the dry reactants include a particulate calcium and/or phosphate reactant having a mean particle size of less than about 8 μm and narrow size distribution. Also provided are the compositions themselves as well as kits for use in practicing the subject methods. The subject methods and compositions produced thereby find use in a variety of applications, including the repair of hard tissue defects, e.g., bone defects.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject methods will be described first, followed by a description of the compositions produced thereby, kits for use in preparing the same and methods for using the subject compositions in methods of hard tissue, e.g. bone repair.

Methods

In the subject methods, dry reactants that include a calcium source and a phosphate source are combined with a setting fluid under conditions sufficient to produce a settable, e.g., flowable, composition that sets into a calcium-phosphate containing product, even when immersed in a fluid environment.

In the subject methods, the dry reactants include a calcium source and a phosphate source. The dry reactants are typically particulate compositions, e.g., powders, where the particle size of the components of the particulate compositions ranges in certain embodiments from about 1 to about 1000 microns, such as from about 1 to about 500 microns and including from about 1 to about 250 microns, as well as from about 1 to about 200 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2 \circ H_2O$); DCPD (dicalcium phosphate dihydrate, brushite or $CaHPO_4 \circ 2H_2O$), ACP (amorphous calcium phosphate or $Ca_3(PO_4)_2H_2O$), DCP (dicalcium phosphate, monetite or $CaHPO_4$), tricalcium phosphate, including both α- and β- $(Ca_3(PO_4)_2$, tetracalcium phosphate $(Ca_4(PO_4)_2O$, etc. In certain embodiments where a calcium phosphate compound is employed, the ratio of calcium to phosphate (i.e. ratio of calcium cations to phosphate groups) of the compound ranges from about 1 to about 2. Calcium sources of interest include, but are not limited to: calcium carbonate $(CaCO_3)$, calcium oxide $(CaO)$, calcium hydroxide $(Ca(OH)_2)$, Dolomite $(CaMgCO_3)$ and the like; Phosphate sources of interest include, but are not limited to: phosphoric acid $(H_3PO_4)$, all soluble phosphates, and the like.

A feature of the subject invention is that the dry reactant portion or component of the cement includes a calcium and/or phosphate dry reactant that has a mean particle size (as determined using the Horiba LA-300 laser diffraction particle sizer (Version 3.30 software for Windows 95)(Irvine, Calif.)) of less than about 8 µm and a narrow particle size distribution (which is referred to below as a fine particle size population). As such, the dry reactant component of the cement, which may include one or more distinct dry reactants, includes a reactant that has a mean particle size of less than about 8 µm and a narrow particle size distribution. The mean particle size of this reactant may vary, ranging in representative embodiments from about 1 to about 7 µm, such as from about 1 to about 6 µm, including from about 1 to about 5 µm, where the mean particle size in certain embodiments may be about 1, about 2, about 3 and about 4 µm, where in certain embodiments the mean particle size is about 3 µm.

This particular reactant of the subject cement compositions is further characterized in that it has a narrow particle size distribution. By narrow particle size distribution is meant that the standard deviation of the particles that make up the particular reactant population (as determined using the Horiba LA-300 laser diffraction particle sizer (Version 3.30 software for Windows 95) (Irvine, Calif.)) does not exceed about 4.0, and in certain representative embodiments does not exceed about 3.0, e.g., does not exceed about 2.5, including does not exceed about 2.0 µm.

This particular reactant of the subject cement compositions is further characterized in that mode (as determined using the Horiba LA-300 laser diffraction particle sizer (Version 3.30 software for Windows 95) (Irvine, Calif.)) does not exceed about 8.0, and in certain representative embodiments does not exceed about 6.0, e.g., does not exceed about 5, including does not exceed about 3.0 µm.

In certain embodiments, the above-described first, reactant makes up the entire dry reactants of the composition, such that it makes up 100% of the dry component of the composition.

In certain embodiments, the dry reactants are further-characterized by including a second reactant that has mean particle size that is at least 2 times larger than the mean particle size of the first reactant component, where the mean particle size of this second reactant may be at least about 9 µm, at least about 10 µm, at least about 20 µm, at least about 25 µm, at least about 30 µm or larger (as determined using the Horiba LA-300 laser diffraction particle sizer (Version 3.30 software for Windows 95) (Irvine, Calif.)), such as at least about 50 µm, at least about 100 µm, at least about 150 µm, at least about 200 µm or higher, where the particle size of the this second population or second reactant (also referred to herein as a coarse particle size population) may range from about 10 to about 500 µm, such as from about 25 to about 250 µm.

In certain embodiments, the amount of the first reactant component of the dry reactant composition is greater than the total amount of other reactant components that may be present, such as the second reactant component as described above. In these embodiments, the mass ratio of the first reactant component to the total mass of the dry reactants may range from about 1 to about 10, e.g., from about 9 to about 6, such as from about 9 to about 7, including from about 9.5 to about 8.5.

In certain representative embodiments, the first reactant component is a calcium phosphate compound having a calcium to phosphate ratio ranging from about 1.0 to about 2.0, including from about 1.33 to about 1.67, such as 1.5. In certain embodiments, the calcium phosphate compound is a tricalcium phosphate, such as α- and β-tricalcium phosphate, where in certain representative embodiments, the tricalcium phosphate is α-tricalcium phosphate.

The first reactant component, as described above, may be prepared using any convenient protocol, including the representative air pulverization protocol is described in greater detail in the Experimental Section below.

A variety of calcium phosphate cement compositions are known to those of skill in the art, and such cements may be readily modified into cements of the subject invention by making one of the dry reactant components thereof (such as the component present in the greatest amount) a dry particulate component having the small mean size and narrow size distribution, as described above. Cement compositions known to those of skill in the art and of interest include, but are not limited to, those described in U.S. Pat. Nos. 6,719,993; 6,375,935; 6,027,742; 6,005,162; 5,997,624; 5,976, 234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference. Additional representative cement compositions that may be readily adapted to the subject invention include, but are not limited to: the cement formulations described in U.S. application Ser. Nos. 10/462,075; 10/629,321; 10/717,171; 10/851,766; 10/661,356; 10/797,907; and 10/850,985; the disclosures of which are herein incorporated by reference.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.33:1.

In certain embodiments where the cement compositions include a combination of coarse and fine particle size dry reactants, the coarse and fine particle size populations may be made up of the same or different compounds, e.g., the same or different calcium minerals, such as the same or different calcium phosphate minerals. For example, in certain embodiments of interest, the cement includes both coarse and fine particle size populations of the same calcium containing mineral, e.g., α-tricalcium phosphate. In yet other embodiments, a portion, if not all of the coarse population of particles is made up of one or more different calcium containing compounds as compared to the compound making up the fine particle size population. For example, in certain embodiments, one may have a fine particle size population made up of a first calcium containing compound, e.g., α-tricalcium phosphate particles, and a coarse particle size population made up of a second calcium containing compound that differs in some way from the compound making up the first population, e.g., in terms of phase, molecular formula, solubility, radioopacity, etc. In certain embodiments, the fine and coarse particle size populations will be made up of different phases of the same calcium containing compound, such as the same calcium phosphate containing compound. For exmample, the coarse and fine particle size populations could both be made up of tricalcium phosphate, but the fine particle size population could be made up of α-tricalcium phosphate while the coarse particle size population is made up of β-tricalcium phosphate particles, such that while the populations are made up of the same compound, they are made up of different phases of the same compound, where the different phases differ from each other at least in terms of solubility. In yet other embodiments, the different populations may be made up of different compounds, e.g., that differ from each other in terms of molecular formula, radioopacity, solubility, combinations thereof, etc. For example, in certain embodiments the fine particle size population is made up of α-tricalcium phosphate particles, and a coarse particle size population is made up at least partially of a different calcium containing compound, e.g., that differs in terms of at least molecular formula, if not radioopacity. For example, the second coarse population of particles may include a calcium containing compound that is not a tricalcium phosphate, such as in those embodiments where the coarse population is made up of a combination of β-tricalcium phosphate particles and particles of dolomite ($CaMgCO_3$).

As indicated above, the subject cement compositions also include a setting fluid, as summarized above. The setting fluid can be any of a variety of setting fluids known to those of skill in the art. Setting fluids include a variety of physiologically compatible fluids, including, but are not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of particular interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0-0.1 to 20%, usually from about 0.01-5 to 15% and more usually from about 5 to 10%.

Representative silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

In certain embodiments, the solution may further include an amount of phosphate ion, as described in U.S. application Ser. No. 10/462,075; the disclosure of which is herein incorporated by reference.

In certain embodiments, the cements may further include an amount of an emulsifying agent, as described in U.S. application Ser. No. 10/ 11/134,051; the disclosure of which is herein incorporated by, reference. Emulsifying agents of interest include, but are not limited to: polyoxyethylene or polyoxypropylene polymers or copolymers thereof, such as polyethylene glycol and polypropylene glycol; nonionic cellulose ethers such as methylcellulose, ethylcellulose, hydroxymethylcellulose, hydroxyethylcellulose, carboxymethylcellulose, carboxyethylcellulose and hydroxypropylcellulose; additional celluloses, such as carboxymethylcellulose sodium, carboxymethylcellulose calcium, carboxymethylstarch; polysaccharides produced by microbial fermentation, such as yeast glucans, xanthan gum, β-1,3-glucans (which may be straight-chained or branched; e.g. curdlan, paramylum, pachyman, scleroglucan, laminaran); other natural polymers, e.g., gum arabic, guar gum, carrageenin, gum tragacanth, pectin, starch, gelatin, casein, dextrin, cellulose; polyacrylamide; polyvinyl alcohol; starch; starch phosphate; sodium alginate and propylene glycol alginate; gelatin; amino-containing acrylic acid copolymers and quaternization products derived therefrom; and the like.

In certain embodiments of particular interest, the emulsifying agent is a cellulose ether, particularly a nonionic cellulose ether, such as carboxymethylcellulose. Carboxymethylcellulose is available from a variety of commercial sources, including but limited to, Sigma, Hercules, Fluka and Noviant. In certain embodiments, the average molecular weight of the cellulose ether is at least about 1000 daltons, such as at least about 5000 daltons, where the average molecular weight may be as high as 10,000 daltons or higher, e.g., 50,000 daltons or higher, 100,000 daltons or higher, and ranges in certain embodiments from about 5,000 to about 100,000 daltons, such as from about 10,000 to about 50,000 daltons.

The proportion of the emulsifying agent in the cement in certain embodiments ranges from about 0.01 to about 10% (w/w), such as from about 0.05 to about 2.0% (w/w).

When employed, the emulsifying agent may be included in one or both of the above liquid and dry reactant components.

In certain embodiments, the cement may further include a contrast or imaging agent, where the contrast agent may be present in one or both of the liquid and dry components, or separate therefrom until combination of all of the components to produce the flowable composition. Contrast agents of interest include, but are not limited to: the water soluble contrast agents described in U.S. application Ser. No. 10/629,321, the disclosure of which is herein incorporated by reference; and the barium apatite contrast agents described in U.S. application Ser. No. 10/851,766, the disclosure of which is herein incorporated by reference.

One or both of the above liquid and dry reactant components may include an active agent that modulates the properties of the product into which the flowable composition prepared by the subject method sets. Such additional ingredients or agents include, but are not limited to: organic polymers, e.g., proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include, but are not limited to: osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g., NaCl, calcium sulfate; sugars, e.g., sucrose, fructose and glucose; pharmaceutically active agents, antibiotics; and the like. Additional active agents of interest include osteoclast induction agents, e.g., RANKL, as described in U.S. patent application Ser. No. 10/717,171, the disclosure of which is herein incorporated by reference.

In practicing the subject methods, suitable amounts of the dry reactants, the setting fluid and the water-soluble contrast agent are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45.

As mentioned above, the requisite amounts of dry reactants and setting fluid are combined under conditions sufficient to produce the flowable product composition. As such, the dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference. Of interest in certain embodiments are the storage/mixing elements disclosed in U.S. Pat. Nos. 6,375,935 and 6,719,993; as well as U.S. application Ser. Nos. 10/462,075; 10/629,321; 10/717,171; 10/851,766; 10/661,356; 10/797,907; and 10/850,985; the disclosures of which are herein incorporated by reference.

The temperature of the environment in which combination or mixing of the dry and liquid components takes place is sufficient to provide for a product that has desired setting and strength characteristics, and typically ranges from about 0 to 50° C., usually from about 20 to 30° C. Mixing takes place for a period of time sufficient for the flowable composition to be produced, and generally takes place for a period of time ranging from about 15 to 120 seconds, usually from about 15 to 100 seconds and more usually from about 15 to 60 seconds, e.g., 15 to 50 seconds, 15 to 30 seconds, etc.

In certain embodiments of the subject invention, vibration is used in conjunction with at least the preparation of the orthopedic cement. By used in conjunction with the preparation of an orthopedic cement is meant that vibration is employed at some point during the period in which the cement precursors of the cement, e.g., liquid and solid reagents or cement components, are combined to produce a flowable cement product composition. With many orthopedic cements of interest, dry and liquid precursors, e.g., a powder and setting liquid, are combined to a produce a flowable cement composition product that, over time, sets into a solid material. In certain embodiments of the subject invention, vibration is employed by applying a vibratory force, e.g., sonic or mechanical, to the precursors of the flowable composition, e.g., during mixing of the precursors. For example, in certain representative embodiments, vibration may be applied to the container or vessel, e.g., syringe, in which the flowable cement composition is prepared, and thereby applied to the flowable cement composition as it is being prepared.

The vibratory force may be characterized in terms of frequency, such as cycles per second (Hertz or Hz), where in certain embodiments the vibratory force applied to an object during the subject methods may have a frequency that ranges from about 0.1 to about 100,000 Hz or higher, including from about 5.0 to about 100,000 Hz or higher, e.g., from about 5.0 to about 50,000 Hz or higher, such as from about 10 to about 35,000 Hz, including from about 20 to about 20,000 Hz. In certain embodiments, the vibratory force has a frequency that is sufficient to provide for the desired outcome, e.g., full delivery of the cement without application of significant backforce (as described in greater detail below) but does not exceed about 10,000 Hz, and in certain embodiments does not exceed about 5000 Hz, and in certain embodiments does not exceed about 100.0 Hz. For example, where the vibratory force applied to an object during the subject methods is a sonic force, the force may be infrasonic or ultrasonic, or in the audible range. The vibratory force may also be characterized in terms of its amplitude or magnitude of vibration. By "amplitude" is meant the movement in any direction. In representative embodiments, the amplitude of the applied, vibratory force will range from about 1 Angstrom to about 2 mm, such as from about 1 to about 500 microns, including from about 10 to 100 microns. In certain embodiments, the amplitude of the applied vibratory force will range from about 1 Angstrom to about 1 mm, such as from about 1 to about 100 microns, including from about 10 to 50 microns. Depending on the application and desired nature of the vibratory force, the direction or orientation of the vibration may vary greatly, where representative orientations include, but are not limited to: circular, unidirectional, random, etc. In some instance, the vibration parameters, e.g., frequency and/or amplitude, may be varied over the course or duration of the vibration usage, as may be desired depending on the particular application being performed.

The vibratory force may be applied to the cement components for the duration of the preparatory time or for a portion thereof, e.g., while the initial components are combined, while additives are combined with the product of mixing of the initial components, etc. In certain representative embodiments, vibration is applied for a duration ranging from about 1 sec to about 5 minutes, such as from about 10 sec to about 1 minute, including from about 15 sec to about 30 sec. Such embodiments are further described in application Ser. Nos. 10/661,356 and 10/797,907; the disclosures of which are herein incorporated by reference.

The above-described protocols result in the production of a flowable composition that, is capable of setting into a calcium phosphate mineral product, as described in greater detail below, where the flowable composition is radioopaque during, at least during implantation.

Settable/Flowable Compositions

The flowable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like compositions, as well as more liquid compositions. As such, the viscosity time of the subject flowable compositions, defined as time periods under which the mixed composition injects through a standard Luer-lok fitting after mixing, typically ranges up to about 10 minutes, usually up to about 7 minutes, such as up to about 4 minutes. Of particular interest in many embodiments are paste compositions that have an injectable viscosity that injects in a time period ranging up to about 5 minutes, such as about up to about 4 minutes. Pastes that stay paste-like for longer period may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.5:1 and more usually from about 1:7:1 to 1.6:1. Of particular interest in many embodiments are apatitic products, which apatitic products have a calcium to phosphate ratio ranging from about 2.0:1 to 1.33:1, including both hydroxyapatite and calcium deficient analogs thereof, including carbonate substituted hydroxyapatite (i.e. dahllite), etc. The subject paste-like composition is, in many embodiments, one that is capable of setting into a hydroxyapatitic product, such as a carbonated hydroxyapatite, i.e. dahllite, having a carbonate substitution of from about 2 to about 10%, usually from about 2 to about 8% by weight of the final product.

The period of time required for the compositions to harden or "set" may vary. By set is meant: the Gilmore Needle Test (ASTM C266-89), modified with the cement submerged under 37° C. physiological saline. The set times of the subject cements may range from about 30 seconds to 30 minutes, and will usually range from about 2 to 15 minutes and more usually from about 4 to 12 minutes. In many embodiments, the flowable composition sets in a clinithlly relevant period of time. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components.

A feature of the rapidly setting compositions is that they rapidly set into a high strength product, as determined by the Gilmore Needle Test (ASTM C266-89) in terms of setting value. More specifically, the compositions attain high strength rapidly, such that they may be viewed as rapid strength attainment compositions. As such, at 3 minutes the compositions have a setting value of at least about 200 Newtons, such as at least about 300 Newtons, where the setting value may be as high as about 400, about 500, about 600 or more Newtons. At 6 minutes the compositions have a setting value of at least about 400 Newtons, such as at least about 500 Newtons, where the setting value may be as high as about 600, about 700, about 800, about 900, about 1000 or more Newtons. A feature of the subject compositions is that they are manipulatable while they are setting into a solid product. As such, they may be manipulated during the setting process without adversely affecting the properties of the final product. For example, during the setting process, screws can be drilled into them, without adversely impacting the properties of the final product.

In certain embodiments, the settable compositions are characterized as compositions that go through the following phases: (1) a working phase in which the composition may be manipulated, e.g., delivered to a bone defect site; (2) a setting phase, in which the composition should be maintained without manipulation; (3) a "drillable" phase, in which hardware, such as screws, may be inserted or positioned into the composition; and (4) a screw tightening phase, in which screws positioned in the composition during the "drillable" phase may be tightened without adversely affecting the composition. In certain embodiments, the working phase ranges from about 0.5 minutes to about 5.0 minutes, e.g., from about 0.5 minutes to about 4.0 minutes following mixing of the components. In certain embodiments, the setting phase ranges from about 1 minute to about 15 minutes, e.g. from about 1 minutes to about 10 minutes following mixing of the components. In certain embodiments the drillable phase commences from about 5 minutes to about 10 minutes following mixing of the components, and may extend to about 10 minutes to about 15 minutes or longer following mixing of the components. In certain embodiments, the screw tightening phase ranges comments from about 10 minutes to about 15 minutes following mixing of the components.

In one representative embodiment, the working phase ranges from about 0 to about 2 minutes, e.g., from about 0.5 to about 1 minute following mixing of the components. In this embodiment, the setting phase occurs during the period from about 1 minute to about 5 minutes following mixing of the components. In this embodiment, the drillable phase begins during the period from about 5 minute to about 10 minutes following mixing of the components. In this embodiment, the screw-tightening phase commences at about 10 minutes following mixing of the components.

In another representative embodiment, the working phase lasts up to about 5 minutes, and usually up to about 4 minutes, including 3 minutes, following mixing of the components. In this embodiment, the setting phase occurs during the period from about 4 minutes to about 10 minutes following mixing of the components. In this embodiment, the drillable phase begins during the period from about 10 minutes to about 15 minutes following mixing of the components. In this embodiment, the screw-tightening phase commences at about 15 minutes following mixing of the components.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the assay described in Morgan, E F et al., 1997, Mechanical Properties of Carbonated Apatite Bone Mineral Substitute: Strength, Fracture and Fatigue Behavior. J. Materials Science: Materials in Medicine. V. 8, pp 559-570., where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high 100 to 200 MPa. In certain embodiments, the resultant product has a tensile strength of at least about 0.5 MPa, such as at least about 1 MPa, including at least about 5 MPa, at least about 10 MPa or more, e.g., from about 0.5 to about 10 MPa, as determined by the tensile strength assay appearing in the Experimental Section, below.

In many embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for at least about 4 months, at least about 6 months, at least about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for at least about 4 months, at least about 6 months, at least about 1 year or longer, e.g., 2.5 years, 5 years, etc.

In certain embodiments of interest, the product that is produced is a composite product, which includes some unreacted particles, e.g., from the coarse population, present in the final product. In certain of the these embodiments where such a cement is implanted into an in vivo site, the unreacted particles may dissolve (e.g., via resorption) over time leaving a porous structure at the implant site, where the porous structure remains until it is remodeled. In certain embodiments, the remaining coarse particles in the composite may have a different radioopicity than the remainder of the product, e.g., where at least a portion of the coarse particles in the cement were dolomite.

In many embodiments, the flowable paste-like composition is capable of setting in a fluid environment, such as an in vivo environment at a bone repair site. As such, the flowable paste composition can set in a wet environment, e.g., one that is filled with blood and other physiological fluids. Therefore, the site to which the flowable composition is administered during use need not be maintained in a dry state.

In certain embodiments, the subject cement compositions may be seeded with any of a variety of cells, as described in published U.S. Patent Application No. 20020098245, the disclosure of which is herein incorporated by reference.

In addition, in certain embodiments the compositions include demineralized bone matrix, which may be obtained typically in a lyophilized or gel form and is combined with the cement composition at some prior to implantation. A variety of demineralized bone matrixes are known to those of skill in the art and any convenient/suitable matrix composition may be employed.

In certain embodiments, the cements may include one or more collections of contrast particles (for example, for use as tracers during use of the cement), e.g., as described in U.S. Pat. No. 6,273,916 or pending U.S. application Ser. Nos. 10/629,31 and 10/851,766; the disclosure of which is herein incorporated by reference.

Applications

The subject methods and compositions produced thereby, as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone.

Other orthopedic applications in which the cements prepared by the subject system find use include, but are not limited to, the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference. In addition to these particular applications described in this U.S. patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference.

Representative applications of interest also include, but are not limited to: those described in U.S. Pat. Nos. 6,375,935 and 6,719,993; as well as U.S. application Ser. Nos. 10/462,075; 10/629,321; 10/717,171; 10/851,766; 10/661,356; 10/797,907; and 10/850,985; the disclosures of which are herein incorporated by reference.

Kits

Also provided are kits comprising the subject cements, where the kits at least include a dry particular composition that can be combined with a liquid to produce a flowable composition, as described above. A feature of the subject kits is that they include a dry reactant component having a small mean particle size and narrow size distribution, as described above. In certain embodiments, the kits further include a liquid component. When both components are present, the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference. In addition to the cement compositions, the subject kits may further include a number of additional reagents, e.g., cells (as described above, where the composition is to be seeded), protein reagents (as described above), and the like.

In certain embodiments, the subject cements may be kilted as described in U.S. Pat. No. 6,273,916, the disclosure of which is herein incorporated by reference, e.g., packaged in a kit with at least two different sterilized pouches (or analogous compartments) of cement that may independently used at the same or different times, where each pouch may include the same or different cement formulation, e.g., where the cements may differ in terms of contrast characteristics.

In certain embodiments, the kits may further include mixing and/or delivery elements, e.g., mortar and pestle, spatula, vibratory elements, etc., which elements find use in, e.g., the preparation and/or delivery of the cement composition.

In addition to above-mentioned components, the subject kits typically further include instructions for using the components of the kit to practice the subject methods. The instructional material may also be instructional material for using the cement compositions, e.g., it may provide surgical techniques and principals for a particular application in which the cement is to be employed. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Systems

Also provided are systems that find use in practicing the subject methods, as described above. The subject systems at least include dry and liquid components of a cement, as described above, and a mixing element. In certain embodiments, the systems may further include additional agents, e.g., contrast agents, active agents, etc., as described above.

The following examples are offered by way of illustration and not by way of limitation.

EXPERIMENTAL

I. Impact of Different Particle Sizes on Cement Function
A. α-Tricalcium Phosphate Preparation:
  The particle size of a starting α-tricalcium phosphate material (TCP) was reduced by two different methods:
    Method 1=ball milling. The resultant ball milled TCP was name "TCP 1."
    Method 2=air pulverization (using a 04-626 Micron Master Jet Pulverizer device obtained from the Jet Pulverizer Company and operated according to the manufacturer's instructions). The resultant air pulverized TCP was name "TCP 2."
These reduction methods resulted in different particle size distributions.
TCP particle size distribution was analyzed using a Horiba LA-300 laser diffraction particle sizer (Version 3.30 software for Windows 95). The particle size distribution resulting from each method of reduction follows:
Particle Size Reduction Method 1 (values in Microns):
  Mean=9.3
  Mode=9.4
  Standard Deviation=6.5
Particle Size Reduction Method 2 (values in Microns):
  Mean=2.9
  Mode=2.4
  Standard Deviation=2.0
B. Cement Formulas:
Cement formulas were investigated consisting of a mixture of α-tri calcium phosphate (TCP1, TCP2), dicalcium phosphate anhydrous (DCPA) and sodium phosphate anhydrous ($NaH_2PO_4$) mixed with dilute sodium silicate (2.5 vol. %, pH=11.0 using a liquid to powder ration of 0.40. The specific formulas were:
i. Cement Formula 1:

| | |
|---|---|
| TCP 1 = | 20 mMoles |
| DCPA = | 7 mMoles |
| $NaH_2PO_4$ = | 0.8 mMoles | ii. Cement Formula 2:

| | |
|---|---|
| TCP 2 = | 20 mMoles |
| DCPA = | 7 mMoles |
| NaH$_2$PO$_4$ = | 0.8 mMoles | iii. Cement Formula 3:

| | |
|---|---|
| TCP 1 = | 16 mMoles |
| TCP 2 = | 3 mMoles |
| DCPA = | 7 mMoles |
| NaH$_2$PO$_4$ = | 0.8 mMoles |

C. Setting Characteristics

The above cement formulations were evaluated in terms of early strength attainment (setting) as measured by a modified Gilmore needle indentation test. The results are provided below:

| Cement Formula # | Indentation Force (N) 3 minutes | Indentation Force (N) 6 minutes | Tensile Strength (Dimetral) MPa |
|---|---|---|---|
| 1 | 77 | 329 | 3.2 |
| 2 | 651 | 986 | 5.1 |
| 3 | 312 | 480 | 3.8 |

II. Cement Formulations
A. Animal Study Cement Formula:
0.1 SPMA
3.5 Dolomite 106-212 μm
3.5 α-TCP 3.5 μm
0.2% CMC
L/S 0.25
B. (β-TCP) Bone Void Filler Formulations of bone void filler were developed that contained β-tricalcium phosphate, while maintaining improved injection and intrusion characteristics achieved with the addition of carboxymethyl cellulose.

The formulations contained varying percentages (by weight) of β-tricalcium phosphate, 106-212 μm particle size range, manufactured by the following procedure:

Formulate 50% Sodium Silicate Solution:

| (to make 60 mL) | |
|---|---|
| 30 mL (v/v) | Deionized water |
| 30 mL (v/v) | Sodium silicate solution |

Combine β-TCP, Graphite, and 50% Sodium Silicate Solution:

| (to make 100 g) | | |
|---|---|---|
| 100 g | β-TCP | |
| 20 g | graphite (20% of weight of β-TCP) | |
| 60 g | 50% sodium silicate solution (in a L:S of 0.50 with dry powders) | |

Sinter β-TCP @1100° C. for 500 minutes, at a ramp rate of 4.5° C./minute.

Formulations with Varying Percentages of β-TCP (all Formulations Fully Injectable)

| Formula | Setting Time | Tensile Strength (24 hours) |
|---|---|---|
| 50% β-TCP<br>0.10 g SPMA<br>3.5 g β-TCP, 106-212 μm<br>3.5 g α-TCP, 3.5 μm<br>0.1% (w/w) cmc, 50k MW<br>0.38 L:S sodium silicate sol, 1/100 | 3 min: 315 Newtons<br>4 min: 526 Newtons<br>6 min: 713 Newtons<br>10 min: 806 Newtons | Mean: 2.346 MPa<br>(n = 6) |
| 40% β-TCP<br>0.10 g SPMA<br>2.00 g β-TCP, 106-212 μm<br>3.00 g α-TCP, 3.5 μm<br>0.2% (w/w) cmc, 50k MW<br>0.38 L:S sodium silicate sol, 1/50 | 3 min: 141 Newtons<br>6 min: 772 Newtons<br>10 min: 1036 Newtons | Mean: 2.440 MPa<br>(n = 3) |
| 25% β-TCP<br>0.10 g SPMA<br>2.00 g β-TCP, 106-212 μm<br>6.00 g α-TCP, 3.5 μm<br>0.2% (w/w) cmc, 50k MW<br>0.38 L:S sodium silicate sol, 1/50 | 3 min: 203 Newtons<br>6 min: 959 Newtons<br>10 min: 1029 Newtons | Mean: 3.231 MPa<br>(n = 4) |

C. Dolomite Containing Formulations (CaMgCO$_3$)

Dolomite was investigated as an alternative to β-TCP to provide for quicker in vivo resorption within a clinically relevant time frame (~6 months), as achieved with the above formulations with varying percentages of β-TCP (all formulations fully injectable) above, but enhanced radioopacity.

| Formula | Setting Time | Tensile Strength (24 hours) |
|---|---|---|
| ~30% Dolomite<br>0.10 g SPMA<br>2.0 g Dolomite, 106-212 μm<br>5.0 g α-TCP, 2 μm<br>0.1% (w/w) cmc, 50k MW<br>0.25 L:S sodium silicate sol, 1/100 | 3 min: 9 Newtons<br>6 min: 1200 Newtons | Mean: 2.428 MPa<br>(n = 4) |
| 50% β-TCP<br>0.10 g SPMA<br>3.5 g β-TCP, 106-212 μm<br>3.5 g α-TCP, 2 μm<br>0.2% (w/w) cmc, 50k MW<br>0.25 L:S sodium silicate sol, 1/100 | 3 min: 26 Newtons<br>6 min: 1216 Newtons<br>10 min: 1582 Newtons | Mean: 1.638 MPa<br>(n = 4) |

III. In Vivo Study of Bone Void Filler having Formulation II.A.
A. Purpose

This study evaluated the biocompatibility, bone resorption, formation, and biomechanical properties of the implanted regions containing a bone void filler having the formulation of II.A, above. Histological, mechanical and crystallographic analyses were performed following implantation in the rabbit femur.

B. Methods

All animal work was performed at an approved animal facility (Covance, Berkley, Calif.) after obtaining animal care approval (IAC #677) for the study protocol. Ten (10) New Zealand white rabbits aged 9-12 months and with body weight of approximately ~3.5 kg were utilized in this study. Animals were housed individually in standard rabbit cages at room temperature, with normal daylight and night cycles. All of the animals were kept under quarantine for a period of 1 week prior to inclusion into the study. The animals were fed with pellet food, and had free access to water throughout the study period. Animals were operated bilaterally and randomly selected hind legs were implanted with bone void filler. All of the animals were sacrificed at 4 weeks. Six (6) animals were used for biomechanical analysis, and 4 animals were used for histological analysis.

i. Surgical Technique

Animals underwent bilateral surgical removal of a 3.2 mm cylindrical core of cancellous bone from the distal femoral metaphysis, and implantation with bone void fillers. Under standard anesthesia (CRP-CA SOP 33101, Covance, Berkley, Calif.) with intravenous medication (Diazepam 0.5 mg/kg, Ketamine 10 mg/kg) the incision sites were shaved and prepared for operation. A closed cavity was created at the end of each femur per animal according to the Pasquier method. Specifically, under general anesthesia, the bilateral knees of the rabbits were prepared using sterile technique, and straight 1 cm incisions were made on the lateral side each distal femur. The tensor fascia lata was dissected longitudinally, and the lateral condyle of the distal femur was exposed. A cortical bone window of 5 by 5 mm square and 0.5 mm in thickness was created and removed temporarily from the lateral femoral condyle, exposing the cancellous bone of the distal metaphysis. Cylindrical cavities 3.2 mm in diameter and approximately 8 mm in length were made by manual, low speed drilling using sterilized saline coolant. Close attention was taken not to penetrate into the medullary canal or joint space. The cavities were irrigated with saline during and after drilling.

The bone void filler was prepared and injected into the void using a 12 gauge needle with retrograde injection technique. Cortical bone plugs were replaced, and the wounds irrigated with saline and sutured. Both AP and Lateral C-arm still photos of the distal femurs were taken immediately following the procedure. Animals were monitored postoperatively until they were able to ambulate, and then returned to their cages. Animals received subcutaneous injections of pain relief medication and routine postoperative antibiotics (Buprenorphine 0.001-0.01 mg/kg and Baytril 5-10 mg/kg) during the immediate postoperative period. Postoperatively, rabbits ambulated freely without knee joint immobilization.

ii. Histological Analysis

Immediately following sacrifice, 4 pairs of bilateral femurs were cleaned of soft tissue and radiographed. After fixation in 10% phosphate neutral formalin solution for three days, the femurs were prepared for histological analysis. Femurs were dehydrated by ethyl alcohol in increasing concentrations from 70% to 100%. The specimens were then infiltrated with PMMA resin and polymerized for approximately two weeks. The undecalcified histological specimens were sliced transversely to the axis of the femur and stained with trichrome.

iii. Biomechanical Testing

Immediately following sacrifice, bilateral femora were cleaned of soft tissue and AP and lateral radiographs were obtained using C-arm Fluoroscopy. Distal femora were cut in two different places perpendicular to the axis of the cylindrical implants. Mid sections of the cut (7 mm in length) were utilized for biomechanical testing. Parallelism was provided by cutting these specimens on the same plane with a slow speed, irrigated saw fitted with a diamond blade (Beuhler Isomet). Mid sections were placed under the material testing machine (5865 Instron testing machine, Canton, Mass.), and an indenter ($7/64$ inch in diameter) was used to apply a compression load to the implanted area. The actuator of the material testing machine was lowered by 0.1 mm/sec for 2.5 mm, and data was collected at every 50 millisecond.

iv. Chemical and Crystallographic Analysis

Fourier transform infrared spectroscopy (FTIR) and powder X-ray diffraction (XRD) analysis were performed on the bone void filler after the sacrificing animals. Samples were extracted from the implant site of three animals-following biomechanical testing. Bone void fillers were easily identifiable within the bone tissue and were extracted by careful dissection and slow drilling of the implant area. Samples were then dried by grinding in acetone to a fine powder.

FTIR was performed on individual samples explanted from separate animals (N=3) by mixing approximately 1±0.6 mg orsample with about 0.3 grams of potassium bromide. 1.3 cm diameter sample pellets using 20,000 lbs load. Spectra were collected from 400 $cm^{-1}$ to 4000 $cm^{-1}$ wavenumber. Spectra are displayed at 400 to 1600 $cm^{-1}$ for clarity of the P—O bands at about 563 and 602 $cm^{-1}$ that correspond to apatite.

For XRD analysis, dried powders were scanned from 10° to 40° 2-theta using Cu k-alpha radiation on a Phillips/Norelco x-ray diffraction system using TXRD software (version 3.7 Tasker Applications). XRD data was compared to ICDD standards for hydroxyapatite (9-432) and the starting reactants alpha-tricalcium phosphate (9-348) and monetite (9-80). Mineralogical analysis procedures for XRD were performed in conjunction with standard equipment operating procedures.

v. Statistical Analysis

Statistical comparisons were performed between the bone void filler and virgin cancellous bone using two-tailed student t-test. The level of statistical significance were set at p=0.05 for all of the analysis.

C. Results i. Histology

Histological analysis results indicated that the bone void filler appeared to be biocompatible and osteoconductive, with the presence of marked bone apposition and no adverse tissue reaction. Remodeling and replacement by newly formed bone was apparent. Normal bone remodeling by osteoclastic cell-mediated resorption and new bone formation around the cylindrical implantation area was also observed. FIG. 1 provides a view of a bone void filler implanted femoral specimen. In FIG. 1, several haversian canals are apparent. Osteoclasts tunneling into the bone void filler are observed. New lamellar bone that has replaced regions of the bone void filler is in direct apposition to the remaining the bone void filler.

ii. Biomechanics

Biomechanical study results indicated that the area implanted with the bone void filler had strength value that were higher than cancellous bone of the same region.

As indicated in histological analysis results, the material went through remodeling Specimens were tested mechanically following in vivo bone remodeling process. The strength of these implanted regions was the result of implanted material that also contained newly formed bone. The strengths of the implanted area were 278 N (±153) and 253 N (±157), respectively. The strength of the virgin cancellous bone of the same implantation area was found to be 130 N (±37). The bone void filler implanted areas were stronger than the cancellous bone of the same area, p=0.024.

iii. Chemistry and Crystallography

Figure 2:
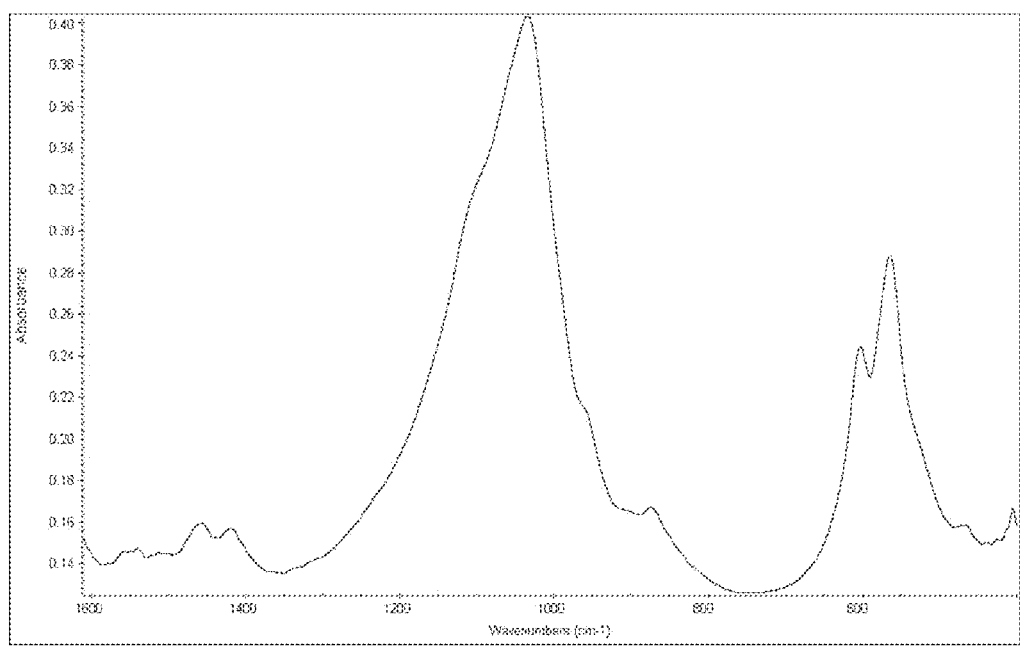
FIG. 2 provides an FTIR spectrum of the cement employed to produce the depicted of FIG. 1.

FTIR results showed that all sample spectra are indicative of low crystalline order carbonated apatite with no evidence of peaks corresponding to other mineral phases. FIG. 2 is a representative FTIR spectrum of the bone void filler demonstrating development of a carbonated apatite following 4 week implantation in the rabbit femur. The spectra shows characteristic apatite absorptions resulting from the P—O bond in phosphate at 1035 cm$^{-1}$ (very strong), 603 cm$^{-1}$ (strong), and 564 cm$^{-1}$ (strong). Also apparent is the characteristic C—O absorption due to carbonate in the apatite lattice at 1456 cm$^{-1}$ (strong), 870 cm$^{-1}$ (shoulder).

Figure 3:
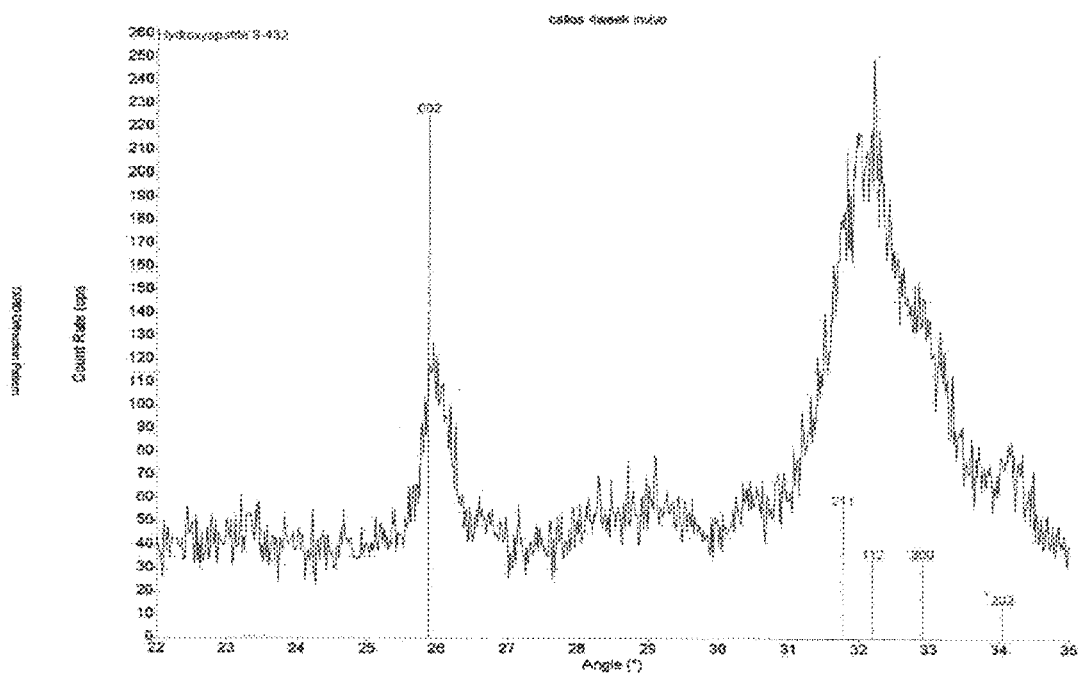
FIG. 3 provides an XRD pattern of the cement employed to produce the depicted in FIG. 1

The x-ray diffraction patterns of the bone void filler is presented in FIG. 3 with the International Center for Diffraction Data (ICDD) "stick" patterns to aid in phase identification. FIG. 3 is an XRD pattern of the bone void filler obtained following in vivo implantation for 4 weeks. The diffraction pattern shows complete conversion to apatite ((ICDD #'s 9-432) with no other mineral phases detected.

D. Discussion and Conclusion

Histological data demonstrated that there was no adverse tissue response from the bone void filler implanted in the rabbit femur. The material appeared to be biocompatible with normal bone healing occurring around the periphery of the cylindrical implant area where the material was resorbed through cell mediated activity and normal bone remodeling. There was complete bone apposition to the bone void filler that was followed by osteoclastic resorption. Subsequent to this resorption, vascular ingrowth and new bone formation was, observed. New bone formation was evidenced by the production of osteoid and by osteoblast cells in direct apposition to the partially resorbed bone void fillers and host bone surfaces.

Biomechanical results demonstrated that the two bone void filler retains strength during the native bone remodeling process and the strength of the implanted area remains similar or higher than the virgin cancellous bone.

It is evident from the above results and discussion that the subject cements having at least one of the reactant components be a reactant with a small mean particle size and narrow particle size distribution provide for a number of beneficial properties. Such properties include, but are not limited to: improved injectability, faster strength attainment in a faster period of time, and an ultimately higher strength attainment. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A flowable composition that sets into a calcium phosphate containing product, wherein said composition is produced by a method comprising:
   combining:
   (a) a setting fluid; and
   (b) a dry reactant component comprising a first particulate calcium and/or phosphate reactant having a mean particle size of less than about 8 μm and narrow particle size distribution;
   in a ratio sufficient to produce said flowable composition.

2. A method of repairing a hard tissue defect, said method comprising:
   applying to the site of said defect a flowable composition that sets into a calcium phosphate containing product, wherein said composition is produced by a method comprising:
   combining:
   (a) a setting fluid; and
   (b) a dry reactant component comprising a first particulate calcium and/or phosphate reactant having a mean particle size of less than about 8 μm and narrow particle size distribution;
   in a ratio sufficient to produce said flowable composition.

3. A kit comprising:
   a dry reactant component comprising a first particulate calcium and/or phosphate reactant having a mean particle size of less than about 8 μm and narrow particle size distribution.

4. The kit according to claim 3, wherein said kit further comprises a second calcium and/or phosphate reactant having a mean particle size that is greater than about 9 μm.

5. The kit according to claim 4, wherein the mass ratio of said first particulate reactant to the total mass of the other dry reactants ranges from about 1 to about 10.

6. The kit according to claim 5, wherein said first particulate calcium and/or phosphate reactant is a calcium phosphate compound.

7. The kit according to claim 6, wherein the ratio of calcium to phosphate of said calcium phosphate compound ranges from about 1 to about 2.

8. The kit according to claim 7, wherein said calcium phosphate compound is a tricalcium phosphate.

9. The kit according to claim 3, wherein said first particulate calcium and/or phosphate reactant has a mean particle size of about 4 μm.

10. The kit according to claim 9, wherein said kit further comprises a setting fluid or components for producing the same.

11. The kit according to claim 10, wherein said setting fluid is a solution of a soluble silicate.

12. The kit according to claim 3, wherein said kit further comprises a mixing element.

13. A system comprising:
   (a) a dry reactant component comprising first particulate calcium and/or phosphate reactant having a mean particle size of less than about 8 μm and a narrow particle size distribution; and
   (b) a setting fluid.

14. The system according to claim 13, wherein said system further comprises a second calcium and/or phosphate particulate reactant having a mean particle size that is greater than about 9 μm.

15. The system according to claim 14, wherein the mass ratio of said first particulate reactant to the total mass of dry reactants ranges from about 1 to about 10.

16. The system according to claim 15, wherein said first particulate calcium and/or phosphate reactant is a calcium phosphate compound.

17. The system according to claim 16, wherein the ratio of calcium to phosphate of said calcium phosphate compound ranges from about 1 to about 2.

18. The system according to claim 17, wherein said calcium phosphate compound is a tricalcium phosphate.

19. The system according to claim 13, wherein said first particulate calcium and/or phosphate reactant has a mean particle size of about 4 μm.

20. The system according to claim 19, wherein said setting fluid is a solution of a soluble silicate.

21. The system according to claim 13, wherein said system further comprises a mixing element.

22. The composition according to claim 1, wherein the dry reactant component further comprises a second particulate calcium and/or phosphate reactant having a mean particle size that is greater than about 9 μm.

23. The composition according to claim 1, wherein the narrow particle size distribution comprises a standard deviation that does not exceed about 4 μm.

24. The composition according to claim 1, wherein the first particulate calcium and/or phosphate reactant comprises a tricalcium phosphate.

25. The composition according to claim 24, wherein the tricalcium phosphate is α-tricalcium phosphate.

26. The composition according to claim 1, wherein the flowable composition has a setting value of at least about 200 Newtons in 3 minutes.

27. The composition according to claim 1, wherein the flowable composition has a setting value of at least about 400 Newtons in 6 minutes.

* * * * *